United States Patent [19]

Eguchi et al.

[11] 4,232,543
[45] Nov. 11, 1980

[54] DEVICE FOR MEASURING THERMAL CONDUCTIVITY OF LIQUIDS

[75] Inventors: Wataru Eguchi, Kyoto; Makoto Harada, Otsu; Masataka Tanigaki; Yutaka Tada, both of Kyoto, all of Japan

[73] Assignee: The President of Kyoto University, Kyoto, Japan

[21] Appl. No.: 68,525

[22] Filed: Aug. 22, 1979

[30] Foreign Application Priority Data

Feb. 28, 1979 [JP] Japan .................................. 54-023050

[51] Int. Cl.$^3$ .......................................... G01N 25/18
[52] U.S. Cl. ...................................... 73/15 A; 73/53
[58] Field of Search ............ 73/15 A, 15 R, 53, 61 R, 73/61 LM

[56] References Cited

FOREIGN PATENT DOCUMENTS 2331280 1/1975 Fed. Rep. of Germany .......... 73/15 A

OTHER PUBLICATIONS

Tada et al., "Laser Flash Method for Measuring Thermal Conductivity . . . ", Rev. Scient. Inst., vol. 49, No. 9.
Schriempf, "A Laser Flash Technique . . . ", High Temp.-High Pressures (GB), vol. 4, No. 4, (1972), pp. 411–416.

*Primary Examiner*—Donald O. Woodiel
*Attorney, Agent, or Firm*—Robert E. Burns; Emmanuel J. Lobato; Bruce L. Adams

[57] ABSTRACT

An apparatus for measuring thermal conductivity of a desired sample liquid, even of a transparent sample liquid, on the basis of thermal diffusion to the sample liquid from a small and thin metal disc which is heated by laser flash. The sample liquid is inserted within a small gap which is formed between the metal disc and a sample holding block, and the thermal diffusion can be measured by a thermocouple connected to the metal disc.

7 Claims, 7 Drawing Figures

F I G. 1
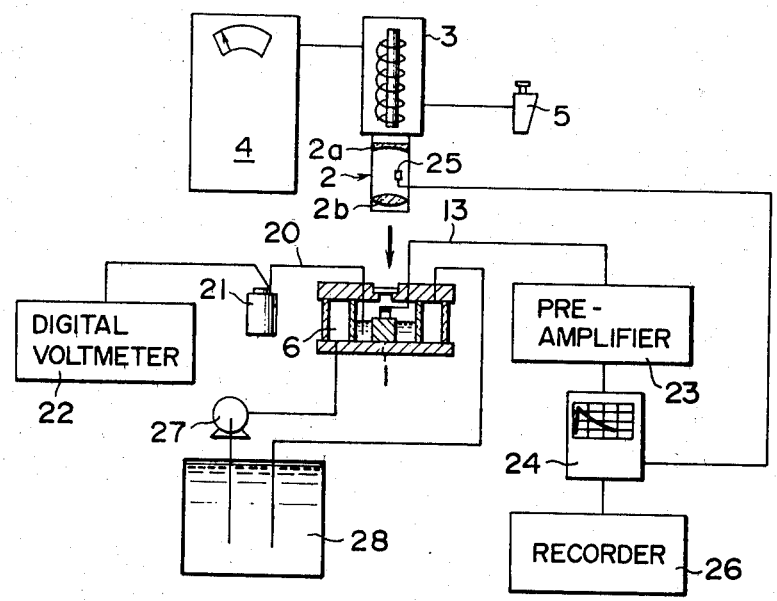
F I G. 2
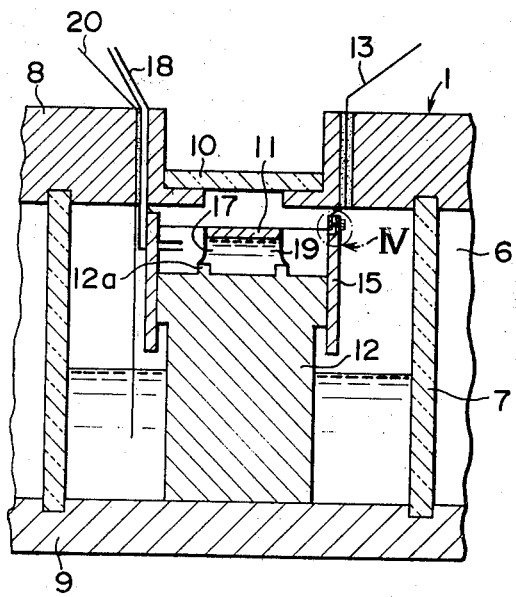

DEVICE FOR MEASURING THERMAL CONDUCTIVITY OF LIQUIDS

BACKGROUND OF THE INVENTION

This invention relates to a device for measuring thermal conductivity of liquids, and more particularly to a thermal conductivity measuring device of the laser flash heating type in which a sample liquid is heated by impulsive light from a laser (laser flash).

In the conventional laser flash heating type measuring device of this class, a sample liquid, for instance, mercury is sealed in a container of boron nitride with a lid of a transparent quartz plate and irradiated from above by a laser flash, while measuring the response in temperature rise at the bottom surface of the sample mercury layer by a thermocouple which has its detecting end at the bottom of the container.

However, such conventional measuring device has the following problems.

(1) The measurement is possible only with an opaque liquid like mercury which is impermeable to laser light and which can receive the energy of the irradiated laser flash at its surface, and not with most of other liquids which are permeable to the laser light.

(2) Where a liquid of good thermal conductivity like a liquid metal is to be measured, it is easy to choose a container material with a thermal conductivity low enough as compared with that of the sample liquid. However, many of other liquids do not have much difference in thermal conductivity from the container which holds the sample, making it difficult to obtain the heat conductivity and thermal diffusivity of a sample from the measurement of temperature response.

(3) It is extremely difficult to seal up the sample liquid in the container and a thin gas absorption layer is apt to be formed between the sample liquid and the wall surfaces of the container, producing a contact resistance which causes unignorable errors to the measured values.

(4) Strict assessment of the thickness of the sample liquid layer is required in analyzing the measured temperature response, so that it is necessary to know precisely the thermal expansion coefficient of the container. In addition, there is a possibility of the sample liquid overflowing from the container or of a void space being formed within the container when the measuring temperature is changed, due to the difference in thermal expansion coefficient between the container material and the sample liquid.

SUMMARY OF THE INVENTION

The present invention contemplates to solve the above-mentioned problems and has as its object the provision of a device which is capable of absolute measurement of thermal conductivity of liquids or liquidus materials, including light permeable liquids with ordinary or relatively low thermal conductivity, in a quick and facilitated manner without use of any reference material and without strict assessment of the thickness of the sample liquid layer.

According to the present invention, there is provided a device for measuring thermal conductivity of liquids, comprising: a thin and small metal disc to be heated by a laser flash; a sample holding block located beneath the metal disc; and a pair of thermocouple wires connected to the metal disc to measure the thermal conductivity of a sample liquid on the basis of thermal diffusion from the metal disc to a cylindrical layer of the sample liquid inserted between the metal disc and the sample holding block; the metal disc being held in a horizontal position by the thermocouple wires and at least one auxiliary support filament.

The thermal conductivity measuring device of the invention has the following effects or advantages.

(1) It becomes possible to make absolute measurement of the thermal conductivity of liquidus materials in general which have thus far been immeasurable, including transparent liquids, electroconductive liquids, and liquids with an ordinary or relatively low thermal conductivity, in a quick and facilitated manner without using any reference material and over a wide temperature range.

(2) The small metal disc is held in a horizontal position by a pair of thermocouple wires and at least one auxiliary support filament, so that the laser light can be applied vertically to the surface of the metal disc. This increases the accuracy of measurement to a considerable degree.

(3) The pair of thermocouple wires have, in addition to the primary sensing function, the function of supporting the metal disc in a horizontal position, contributing to reduce the number of required component parts as well as the production cost.

BRIEF DESCRIPTION OF THE DRAWINGS

The accompanying drawings show by way of example a preferred embodiment of the present invention, in which:

FIG. 1 is a diagrammatic view showing the general arrangement of the thermal conductivity measuring device according to the present invention;

FIG. 2 is a vertical sectional view of a sample chamber;

DESCRIPTION OF PREFERRED EMBODIMENT

Figure 3:
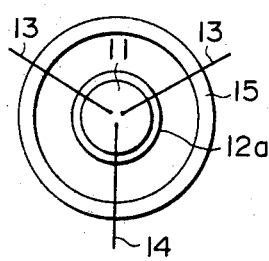
FIG. 3 is a plan view of a small metal disc which is supported in a horizontal position.

Referring to FIG. 1, the thermal conductivity measuring device of the invention includes a sample chamber 1 and, overhead the sample chamber 1, a pulse ruby laser beam generator 3 with a laser beam magnifier 2. The pulse ruby laser beam generator 3 has a maximum output of 3J and irradiates the sample chamber 1 with an impulsive laser light from a monochrystalline ruby rod which is excited by discharging the electric energy charged in a high voltage condenser 4 to a xenon lamp through a remote switch 5.

The diameter of the radiated laser light is magnified about 1.3 times by the laser beam magnifier 2.

The laser beam magnifier 2 consists of a combination of a concave lens 2a and a convex lens 2b and is necessary for ensuring the energy irradiation of uniform density.

The sample chamber 1 is provided with a glass cylinder 7 which has around its circumference a jacket 6 of a constant temperature heat transfer medium as shown in FIG. 2. The upper and lower ends of the glass cylinder 7 are hermetically closed by metal covers 8 and 9, respectively.

The upper metal cover 8 is centrally provided with a circular optical glass window 10 to allow passage therethrough of the laser light.

Located beneath the optical glass window 10 is a thin and small metal disc 11 (a copper disc of 0.65 cm in diameter and 0.0247 cm in thickness or a nickel disc of 0.0236 cm in thickness) to be heated by the laser flash which is passed through the optical glass window 10. A sample holding block 12 having on its top surface an annular projection 12a of 6 mm in inside diameter is located beneath the small metal disc 11 in coaxial relation therewith.

As shown in FIGS. 2 and 3, a pair of thermocouple wires 13 are connected by spot welding to the surface of the small metal disc 11 for the temperature detection. The small metal disc 11 is supported in a level or horizontal position by the thermocouple wires 13 and an auxiliary support wire or filament 14.

Figure 4:
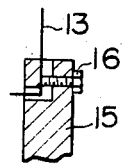
FIG. 4 is a sectional view, on an enlarged scale, of the portion indicated by VI in FIG. 2.

In order to hold the small metal disc 11 in a level position, the metal wires and filament 13 and 14 (0.05 mm in diameter) which are spot-welded to the metal disc 11 are tensioned and clamped by screws 16 to a ring member 15 which is fitted around the sample holding block 12, as shown in FIG. 4. Thus, the small metal disc 11 is supported horizontally over the sample holding block 12 by the three metal filaments 13 and 14.

As seen in FIG. 2, the underside of the metal disc 11 is spaced from the top end of the annular projection 12a on the sample holding block 12 by a gap 17 of 1 to 2 mm in width. It is suitable for the gap 17 to be of such width for forming a cylindrical liquid layer 19 which has the same diameter as the metal disc 11.

A sample liquid to be measured is filled into the gap 17 through a filling tube 18 which opens into the gap 17. When a predetermined quantity of a sample liquid is supplied to the gap 17 through the filling tube 18, the sample liquid fills the gap 17 by its own surface tension, forming a cylindrical liquid layer 19 of the same diameter as the metal disc 11.

In this manner, the liquid layer 19 is interposed between the two metal components 11 and 12, all sides of the liquid layer 19 being exposed to a gas atmosphere. The gas atmosphere is saturated with vapors of a liquid same as the sample at the measuring temperature in order to preclude losses due to evaporation. For this purpose, the lower portion of the glass cylinder 7 is filled with a sufficiently greater amount of the same liquid as compared with that of the sample.

The temperature of the sample chamber including the saturating liquid is measured by a thermocouple 20 which is connected to a zero-calibrating ice jar 21 and a digital voltmeter 22 as shown in FIG. 1.

The signal detected by the thermocouple 13 is amplified by a pre-amplifier 23 and then stored in a high speed digital memory 24.

The above-mentioned digital memory 24 includes a memory to be used for the measurement of response in a short time period (0 to 50 ms) and a memory for the measurement of response in a longer time period (0 to 5 s), thereby to improve the accuracy of measurement of the initial response during measurement of response of a long time period and to allow integration of data while checking for presence of any heat radiation.

In FIG. 1, the reference numeral 25 denotes a triggering photodiode which starts digital memory 24 upon detection of the laser light and which is located between the concave lens 2a and convex lens 2b of the laser beam magnifier 2.

Designated at 26 is a recordor which later records the temperature response which has been stored in the digital memory 24, at 27 is a pump, and at 28 is a vessel of the constant temperature heat transfer medium. The constant temperature heat transfer medium, for example, constant temperature water is circulated from the constant temperature bath 28 to the jacket 6 of the sample chamber 1 by the pump 27 to control the temperature of the sample chamber 1.

Alumel-chromel thermocouples are used for the thermocouples 13 and 20.

When using the measuring device of the above construction for the measurement of thermal conductivity of a liquid, the laser light is sighted at the small metal disc 11 through the optical glass window 10 and the sample chamber 1 is set in position prior to the measurement.

Thereafter, the sample chamber 1 is replaced by an inert gas which is admitted thereinto through a liquid inlet which is not shown. At this time, the gas within the sample chamber 1 is discharged through the liquid filling tube 8.

The replacement by an inert gas may be omitted where the sample chamber 1 may be filled with air.

A liquid of the same kind as the sample liquid is then charged into the sample chamber 1 as shown in FIG. 2 through the above-mentioned liquid inlet, and the pump 27 is started to circulate the constant temperature heat transfer medium from the constant temperature bath 28 to the jacket 6 of the sample chamber 1, maintaining the interior of the sample chamber 1 at a predetermined measuring temperature.

As a result, an inert gas atmosphere is created in the upper space of the sample chamber 1, which is saturated with vapors of the liquid same as the sample.

The remote switch is then actuated to excite the ruby laser beam generator 3 by the electric energy charged in the high voltage condenser 4, generating impulsive laser light.

The incident laser light is detected by the photodiode 25 and a trigger signal is fed to the high speed digital memory 24.

In this instance, the laser light from the ruby laser beam generator 3 undergoes diametral magnification through the laser beam magnifier 3, so that only the center portion of the beam with uniform surface density of energy is passed through the window 10 to irradiate the upper surface of the metal disc 11.

Figure 5:
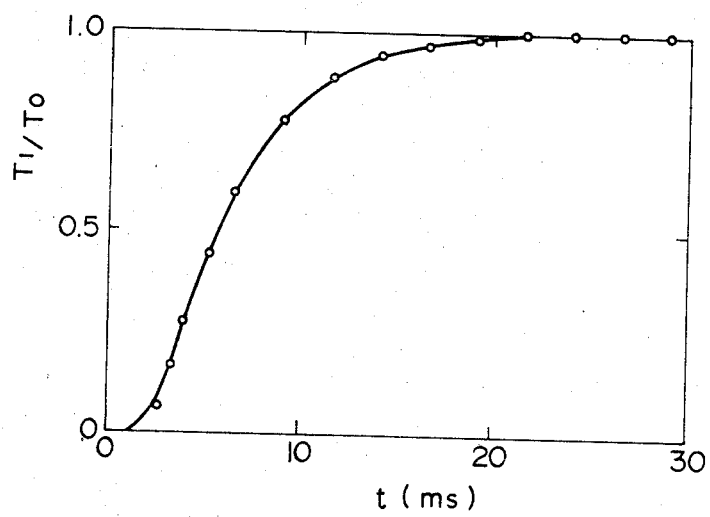
FIG. 5 is a graph showing the temperature response at the under surface of the metal disc.

It has been confirmed by an experiment that the center portion of the diametrally magnified laser beam has a uniform surface density of energy. The experiment was directed to the study of temperature response at the back side of the metal disc 11 which is irradiated by the laser beam. As a result, there was obtained a response curve (FIG. 5) which monotonously converged to a maximum value without showing any locally increased values.

It is known from the curve that the incident energy density in the center portion of the laser beam is uniform and it becomes possible to make data analysis on the basis of the principle of measurement of one dimensional thermal flow (which will be discussed hereinlater).

Upon irradiation by the laser light with uniform surface density of energy, the upper surface of the metal disc 11 is heated instantaneously but the head rapidly diffuses over the entire body of the metal disc 11. As a result, the surface temperature of the metal disc 11 drops quickly and the disc 11 becomes to have a uniform temperature within an extremely short period of time of less than 10 ms. Therefore, the heat radiation of the metal disc to the ambient atmosphere during such a short time period can be ignored.

Thereafter, the heat accumulated in the metal disc 11 is radiated to the ambient atmosphere very slowly, lowering the temperature of the disc 11 little by little.

The changes in the surface temperature of the metal disc 11 after the irradiation by the laser light are detected by the thermocouples 13, which are spot-welded to the upper surface of the metal disc 11, and the detected signals are amplified by the preamplifier 23 and stored in the digital memory 24. The stored temperature response is recorded by the recorder 26. The records of such measurement are plotted by the upper curve a of FIG. 6.

Since the temperature of the sample chamber 1 is maintained constant by the circulation of the constant temperature heat transfer medium to the jacket 6, the temperature of the metal disc 11 returns to the level same as the sample chamber 1.

Under these circumstances, a syringe type liquid injector (not shown) is attached to the outer end of the liquid filling tube 18 which is led out of the sample chamber 1, and a predetermined quantity of the sample liquid is injected into the annular projection 12a on the sample holding block 12, forming a cylindrical liquid layer 19 which fills the gap 17 between the metal disc 11 and the holding block 12.

In some case, the lower portion of the liquid layer 19 does not take a perfect cylindrical form due to the surface tension of the sample liquid and the wettability of the material of the holding block with the liquid. However, it suffices if the upper portion of the liquid layer 19, about 1 mm from the under surface of the metal disc 11, is in the cylindrical form.

The cylindrical liquid layer 19 thus formed beneath the metal disc 11 is left to stand for some time until the liquid layer equilibrates with the temperature of the sample chamber 1.

Then, the laser is flashed in the same manner as described hereinbefore when the liquid layer 19 is not yet formed beneath the metal disc 11, measuring the surface temperature response of the metal disc 11. In this instance, the heat which is instantaneously accumulated in the metal disc 11 is radiated into the liquid below, the temperature of the metal disc 11 dropping acceleratedly as compared with a case where no liquid layer exists beneath the metal disc 11.

Figure 6:
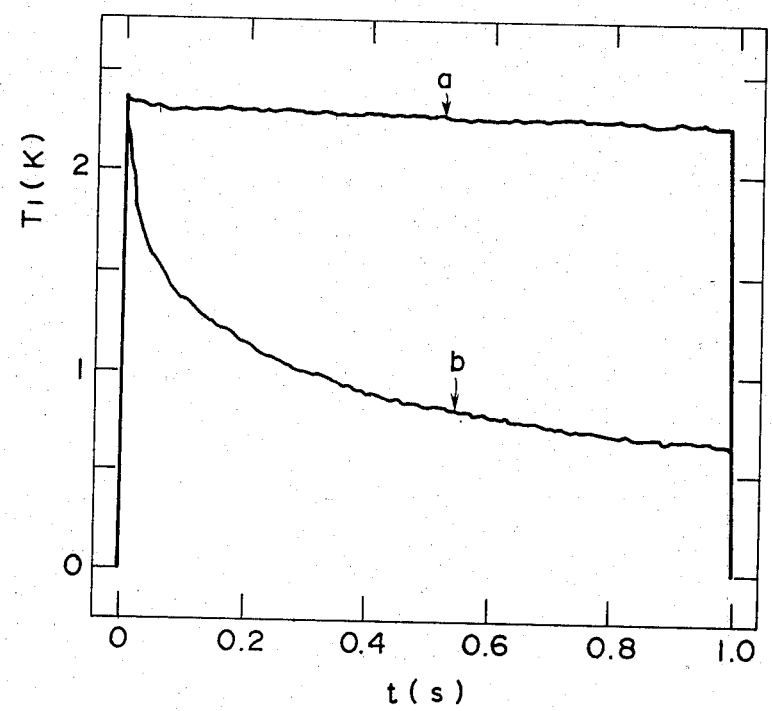
FIG. 6 is a graph showing the temperature response at the upper surface of the metal disc.

FIG. 6 show by way of example a plot b of temperature response as measured by forming a cylindrical liquid layer 19 of distilled water between the metal disc 11 and the sample holding block 12.

By analyzing the differences between the plots a and b, we can obtain the heat radiation by conduction, that is to say, the thermal conductivity of the sample liquid on the basis of the thermal diffusion from the metal disc 11 to the sample liquid.

Given hereinbelow is a practical procedure for obtaining the thermal conductivity of a liquid, treating the thermal flow as a problem of one dimentional diffusion.

Figure 7:
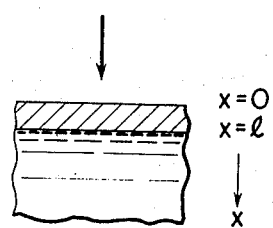
FIG. 7 is a diagrammatic view employed to show the function of the metal disc.

As shown in FIG. 7, if the metal disc 11 is considered as a first layer, a distance measured downwardly from the upper surface of the metal disc 11 is x, the thickness of the metal disc 11 is l, the cylindrical liquid layer 19 is considered as a second layer, and the gas layer above the first layer is considered as a third layer, we obtain the equations for the temperature responses at the upper and lower surfaces of the first layer (metal disc 11) or at $x=0$ and $x=l$ from the equation of thermal diffusion, initial condition and boundary condition, as follows.

$$\frac{T_1(0,t)}{T_0} = \int_0^t \tilde{f}(t-\tau) F_1(0,\tau) d\tau \tag{1-a}$$

$$F_1(0,\tau) = \frac{1}{\pi^{\frac{1}{2}}} \left(\frac{l^2}{\alpha_1 \tau}\right)^{\frac{1}{2}} \left[\frac{1}{1+H_2} + \frac{2}{(1-H_2)(1+H_2)} \times \sum_{n=1}^{\infty} \left(\frac{1-H_1}{1+H_1}\right)^n \left(\frac{1-H_2}{1+H_2}\right)^n \exp\left(-\frac{n^2 l^2}{\alpha_1 \tau}\right)\right] \tag{1-b}$$

$$\frac{T_1(l,t)}{T_0} = \int_0^t \tilde{f}(t-\tau) F_1(l,\tau) d\tau \tag{2-a}$$

$$F_1(l,\tau) = \frac{1}{\pi^{\frac{1}{2}}} \left(\frac{l^2}{\alpha_1 \tau}\right)^{\frac{1}{2}} \frac{2}{(1+H_1)(1+H_2)} \times \sum_{n=0}^{\infty} \left(\frac{1-H_1}{1+H_1}\right)^n \left(\frac{1-H_2}{1+H_2}\right)^n \exp\left[-\frac{(2n+1)^2 l^2}{4\alpha_1 \tau}\right] \tag{2-b}$$

where $$H_1 = \left(\frac{\lambda_2 \rho_2 c_{p2}}{\lambda_1 \rho_1 c_{p1}}\right)^{\frac{1}{2}} \tag{3}$$

$$H_2 = \left(\frac{\lambda_3 \rho_3 c_{p3}}{\lambda_1 \rho_1 c_{p1}}\right)^{\frac{1}{2}} \tag{4}$$

$$T_0 = \left(\frac{Q}{\rho_1 c_{p1} l}\right) \tag{5}$$

$$\tilde{f}(t) = f(t)/Q \tag{6}$$

$$Q = \int_0^\infty f(t) dt \tag{7}$$

In the foregoing formulas, $T_1(x, t)$ is the difference between the temperature of the first layer at the distance x and at the time t and the temperature prior to the measurement, $\lambda_1$, $\lambda_2$ and $\lambda_3$ are the thermal conductivity of the first to third layers, respectively, $\alpha_1$, $\alpha_2$ and $\alpha_3$ are the thermal diffusivity of the first to third layers, respectively, and f(t) is a function which stands for the amount of energy as absorbed by unit area of the upper surface of the first layer.

Further, $C_{p1}$, $C_{p2}$ and $C_{p3}$ are the specific heat capacity of the first to third layers, respectively, $\rho_1$, $\rho_2$ and $\rho_3$ are the density of the first to third layers, respectively, and $T_0$ is a temperature rise which occurs on the assumption that the heat input to the first layer is uniformly stored therein without any scattering.

In the initial response, the equations (1-a), (1-b), (2-a) and (2-b) can be approximated by equations (8-a) and (9-a) under the condition of (8-b) and (9-b).

$$\frac{T_1(0,t)}{T_0} = \frac{1}{\pi^{\frac{1}{2}}} \cdot \frac{1}{1+H_2} \int_0^t \left(\frac{l^2}{\alpha_1 \tau}\right)^{\frac{1}{2}} \tilde{f}(t-\tau) d\tau \tag{8-a}$$

where $$\exp\left(-\frac{l^2}{\alpha_1 t}\right) < \left(\frac{1+H_1}{1-H_1}\right)\left(\frac{1+H_2}{2}\right) \tag{8-b}$$

-continued $$\frac{T_1(l,t)}{T_0} = \frac{2}{\pi^{\frac{1}{2}}} \cdot \frac{1}{(1 + H_1)(1 + H_2)} \int_0^t \left(\frac{l^2}{\alpha_1 \tau}\right)^{\frac{1}{2}} \times \exp\left(-\frac{l^2}{4\alpha_1 \tau}\right) \widetilde{f}(t - \tau) d\tau \quad (9\text{-a})$$

where $$\exp\left(-\frac{2l^2}{\alpha_1 t}\right) < \left(\frac{1 + H_1}{1 - H_1}\right)\left(\frac{1 + H_2}{1 - H_2}\right) \quad (9\text{-b})$$

After the initial response, the following approximation can be established for the equations (1) and (2).

$$\frac{T_1(0,t)}{T_0} = \frac{T_1(l,t)}{T_0} = \exp(h^2 t)\, \mathrm{erfc}(h\, t^{\frac{1}{2}}) \quad (10)$$

where $$h = h_1 + h_2 \quad (11)$$

$$h_1 = \frac{(\lambda_2 \rho_2 c_{p2})^{\frac{1}{2}}}{\rho_1 c_{p1} l} \quad (12\text{-a})$$

$$h_2 = \frac{(\lambda_3 \rho_3 c_{p3})^{\frac{1}{2}}}{\rho_1 c_{p1} l} \quad (12\text{-b})$$

The foregoing proximate analysis shows that the thermal conductivity of the second liquid layer can be obtained by measuring the temperature drop $T_1(0, t)$ at the upper surface of the second layer and applying the measured value to the equation (10).

When determining the thermal conductivity $\lambda_2$ by the equation (10), the thermal conductivity $\lambda_1$ of the first layer is not required.

The table below show by way of example the results of measurement conducted on water and toluene.

| Sample | Measuring Temp. (K.) | Metal Disc (thickness:mm) | Thermal Conductivity (W/(cm. K.)) | |
|---|---|---|---|---|
| | | | Actual Value | Recommended Value |
| Water | 313.6 | Copper (0.25mm) | $1.48 \times 10^{-3}$ | $1.51 \times 10^{-3}$ |
| Toluene | 295.4 | Copper (0.24mm) | $3.29 \times 10^{-3}$ | $3.23 \times 10^{-3}$ |

The re-emergent accuracy of the measurement is 2% which is slightly lower than the value as obtained by carefully conducting the measurement by an ordinary method. However, the ordinary method is a relative measurement using a reference material, while the measurement of the present invention is an absolute measurement which involves less errors in the measured values. The measurement according to the present invention is simple and quick, in contrast to the ordinary method which requires much experience and takes a long time.

Thus, in the measuring device of the present invention, a cylindrical liquid layer 19 is formed in a 1-2 mm wide gap between the horizontally supported metal disc 11 and the sample holding block 12 and the metal disc is flash-heated, measuring the downward heat radiation in less than one second. Since the temperature rise at the back side of the metal disc 11 is 2K at maximum, the convection within the sample liquid during the measuring time can be totally ignored.

The metal disc 11 and the sample liquid beneath the disc are surrounded by a gaseous phase, so that the data of measurement can be analyzed as one dimentional conduction of heat flows as long as the liquid layer 19 is in the form of a cylinder of the diameter same as the metal disc 11. If the measuring time is set such that the depth of heat penetration into the liquid during the measuring time is smaller than the thickness of the liquid layer 19, the thermal conductivity $\lambda_2$ of the sample liquid can be obtained regardless of the thickness of the liquid layer 19 or the thermal conductivity of the sample holding block.

In addition, is a metal disc 11 of a suitable thickness is selected, the thermal conductivity of the liquid can be obtained very easily since the temperature response at the upper surface of the metal disc 11 becomes to have no relation with its thermal conductivity $\lambda_1$ upon lapse of initial several milliseconds.

Moreover, the gas atmosphere of the sample chamber 1 which contacts the circumference of the liquid layer 19 sandwitched between the metal disc 11 and the holding block 12 is saturated with vapors of the same liquid and an inert gas is sealed in the sample chamber 1 to maintain its full pressure higher than the saturated vapor pressure. Therefore, although the temperature of the layer of the metal disc 11 above the sample liquid is increased by about 2K immediately after initiation of the measurement, the temperature increase of such an extent does not brings about any significant evaporation of the sandwitched liquid which would cause errors to the measurement of the temperature response.

The effects of the heat radiation from the upper surface of the metal disc 11 to the gas atmosphere can be easily compensated by the data of measurement of the temperature response where the liquid layer is absent.

Thus, the device of the present invention is capable of accurate measurement of the thermal conductivity of liquids in a quick and facilitated manner, without the difficulties as experienced with the conventional measuring devices.

In the foregoing embodiment, the small metal disc 11 is shown as being supported in a horizontal position by a pair of thermocouple wires 13 and a single auxiliary support filament 14. However, the metal disc 11 may be supported by a pair of thermocouple wires 13 and more than one auxiliary support filament or another thermocouple wire may be employed to replace the auxiliary filament.

It has been confirmed by experiments that the loss of heat through the supporting metal wires is of an ignorable amount.

What is claimed is:

1. A device for measuring thermal conductivity of liquids, comprising:

a thin and small metal disc to be heated by a laser flash;

a sample holding block located beneath said metal disc; and a pair of thermocouple wires connected to said metal disc to measure the thermal conductivity of a sample liquid on the basis of thermal diffusion from said metal disc to a cylindrical layer of said sample liquid inserted between said metal disc and said sample holding block;

said metal disc being supported in a horizontal position by said pair of thermocouple wires and at least one auxiliary support filament.

2. A device as set forth in claim 1, further comprising a laser beam magnifier provided for diametrally magnifying a heating laser beam to ensure uniform density of energy incident on said metal disc and consisting of a combination of a concave lens and a convex lens.

3. A device as set forth in claim 1, wherein said sample holding block is provided with an annular projection on the top surface thereof in coaxially opposing relation with said metal disc.

4. A device as set forth in claim 1, wherein said metal disc is supported on said sample holding block through said pair of thermocouple wires and an auxiliary filament.

5. A device as set forth in claim 1, further comprising a liquid filling tube for inserting a sample liquid between said metal disc and said sample holding block.

6. A device as set forth in claim 1, wherein said metal disc and said sample holding block are placed in a sample chamber capable of producing an inert atmosphere saturated with vapors of a liquid same as said sample liquid.

7. A device as set forth in claim 5, wherein said liquid filling tube is arranged to serve also as an exhaust pipe for the replacement of the atmosphere gas of said sample chamber.

* * * * *